US00PP25098P2

(12) United States Plant Patent
Verhoef

(10) Patent No.: US PP25,098 P2
(45) Date of Patent: Nov. 25, 2014

(54) *SPIRAEA* PLANT NAMED 'VERSPI 1'

(50) Latin Name: *Spiraea nipponica*
Varietal Denomination: Verspi 1

(71) Applicant: Gijsbertus Verhoef, Hazerswoude (NL)

(72) Inventor: Gijsbertus Verhoef, Hazerswoude (NL)

( * ) Notice: Subject to any disclaimer, the term of this patent is extended or adjusted under 35 U.S.C. 154(b) by 131 days.

(21) Appl. No.: 13/694,555

(22) Filed: Dec. 12, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. A. Whealy

(57) ABSTRACT

A new and distinct cultivar of *Spiraea* plant named 'Verspi 1', characterized by its compact and mounding plant habit; vigorous growth habit; freely branching habit; yellow green and lighter bright yellow green variegated leaves; numerous white-colored flowers; and good garden performance.

1 Drawing Sheet

Botanical designation: *Spiraea nipponica.*
Cultivar denomination: 'VERSPI 1'.

BACKGROUND OF THE INVENTION

The present invention relates to a new and distinct cultivar of *Spiraea* plant, botanically known as *Spiraea nipponica* and hereinafter referred to by the name 'Verspi 1'.

The new *Spiraea* plant is a naturally-occurring branch mutation of *Spiraea nipponica* 'Halward's Silver', not patented. The new *Spiraea* plant was discovered and selected by the Inventor on a single plant within a population of plants of 'Halward's Silver' in a controlled outdoor nursery environment in Hazerswoude-Dorp, The Netherlands.

Asexual reproduction of the new *Spiraea* plant by softwood cuttings in a controlled greenhouse environment in Hazerswoude-Dorp, The Netherlands has shown that the unique features of this new *Spiraea* plant are stable and reproduced true to type in successive generations of asexual reproduction.

SUMMARY OF THE INVENTION

Plants of the new *Spiraea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Verspi 1'. These characteristics in combination distinguish 'Verspi 1' as a new and distinct *Spiraea* plant:

1. Compact and mounding plant habit.
2. Vigorous growth habit.
3. Freely branching habit.
4. Yellow green and lighter bright yellow green variegated leaves.
5. Numerous white-colored flowers.
6. Good garden performance.

Plants of the new *Spiraea* can be compared to plants of the mutation parent, 'Halward's Silver'. Plants of the new *Spiraea* differ primarily from plants of 'Halward's Silver' in foliage color as plants of 'Halward's Silver' have solid green-colored leaves.

Plants of the new *Spiraea* can be compared to plants of the *Spiraea japonica* 'Snowmound', not patented. Plants of the new *Spiraea* differ from plants of 'Snowmound' in the following characteristics:

1. Plants of the new *Spiraea* are shorter and more compact than plants of 'Snowmound'.
2. Plants of the new *Spiraea* and 'Snowmound' differ in leaf color as plants of 'Snowmound' have bluish green-colored leaves.

BRIEF DESCRIPTION OF THE PHOTOGRAPH

The accompanying colored photograph illustrates the overall appearance of the new *Spiraea* plant showing the colors as true as it is reasonably possible to obtain in colored reproductions of this type. Colors in the photograph may differ slightly from the color values cited in the detailed botanical description which accurately describe the colors of the new *Spiraea* plant. The photograph is a close-up view of a typical flowering plant of 'Verspi 1'.

DETAILED BOTANICAL DESCRIPTION

The aforementioned photograph and following observations, measurements and values describe plants of the new *Spiraea* grown during the summer in one-gallon containers in an outdoor nursery in Grand Haven, Mich. and under cultural practices which approximate commercial *Spiraea* production. Plants were one year old when the photograph and the description were taken. In the description, color references are made to The Royal Horticultural Society Colour Chart, 2001 Edition, except where general terms of ordinary dictionary significance are used.

Botanical classification: *Spiraea nipponica* 'Verspi 1'.

Parentage: Naturally-occurring branch mutation of *Spiraea nipponica* 'Halward's Silver', not patented.

Propagation:

*Type*.—By softwood cuttings.

*Time to initiate roots, summer*.—About 20 days at 20° C.

*Time to produce a rooted young plant, summer*.—About two months at 20° C.

*Root description*.—Fine, fibrous.

*Rooting habit*.—Freely branching; dense.

Plant description:

*Plant form and growth habit*.—Perennial shrub; compact and mounding plant habit; vigorous growth habit; moderately rapid to rapid growth rate.

*Branching habit*.—Freely branching habit with about numerous lateral branches developing per plant; pinching (removal of terminal apices) enhances lateral branch development.

*Plant height*.—About 75 cm to 100 cm.

*Plant diameter* (*area of spread*).—About 75 cm to 125 cm.

Lateral branch description:

*Length*.—About 25 cm.

*Diameter*.—About 2 mm.

*Internode length*.—About 2 cm.

*Texture*.—Smooth, glabrous.

*Aspect*.—Erect to about 40° from vertical.

*Color, developing*.—Close to 150D tinted with close to 42A.

*Color, developed*.—Close to 165A.

Foliage description:

*Arrangement*.—Alternate, simple.

*Length*.—About 2.7 cm.

*Width*.—About 1.3 cm.

*Shape*.—Elliptic to oblanceolate.

*Apex*.—Broadly acute to obtuse.

*Base*.—Cuneate to obtuse.

*Margin*.—Towards the apex, lobed; towards the base, mostly entire; developing leaves, undulate.

*Texture, upper and lower surfaces*.—Smooth, glabrous.

*Venation pattern*.—Pinnate.

*Color*.—Developing leaves, upper surface: Close to 151D. Developing leaves, lower surface: Close to 2C. Fully expanded leaves, upper surface: Close to 146B; random speckles and sectors, close to 150A; venation, close to 146B or 150A. Fully expanded leaves, lower surface: Close to 138B; venation, close to 138B.

*Petiole*.—Length: About 3 mm. Diameter: About 1 mm. Texture, upper and lower surfaces: Smooth, glabrous. Color, upper and lower surfaces: Close to 144C.

Flower description:

*Flower appearance and arrangement*.—Single rotate flowers arranged in terminal corymbs; freely flowering habit with usually about 15 flowers developing per inflorescence; flowers face upright to outwardly.

*Natural flowering season*.—Continuous flowering during the late spring in Grand Haven, Mich.

*Flower longevity*.—Flowers last about four to six weeks on the plant; flowers not persistent.

*Fragrance*.—None detected.

*Inflorescence height*.—About 1.25 cm.

*Inflorescence diameter*.—About 2.5 cm.

*Flower diameter*.—About 1 cm.

*Flower length* (*height*).—About 3 mm.

*Flower buds*.—Length: About 2 mm. Diameter: About 2 mm. Shape: Globose. Color: Close to 155D.

*Petals*.—Quantity per flower: Single whorl of five petals. Length: About 4 mm. Width: About 4 mm. Shape: Rounded. Apex: Obtuse to slightly retuse. Margin: Entire. Texture, upper and lower surfaces: Smooth, glabrous. Color: When opening, upper and lower surfaces: Close to 155D. Fully opened, upper and lower surfaces: Close to 155D.

*Sepals*.—Quantity per flower: Single whorl of five sepals. Length: About 2 mm. Width: About 1 mm. Shape: Lanceolate. Apex: Acute. Base: Fused. Margin: Entire. Texture, upper and lower surfaces: Smooth, glabrous. Color: When opening, upper and lower surfaces: Close to 144B. Fully opened, upper and lower surfaces: Close to 144B.

*Peduncles*.—Length: About 2 mm. Diameter: Less than 1 mm. Strength: Strong. Aspect: Mostly erect. Texture: Smooth, glabrous. Color: Close to 145B.

*Pedicels*.—Length: About 1 cm. Diameter: Less than 1 mm. Strength: Strong. Aspect: Erect to about 40° from peduncle axis. Texture: Smooth, glabrous. Color: Close to 145B.

*Reproductive organs*.—Androecium: Quantity per flower: About five to ten. Anther shape: Globular. Anther length: Less than 1 mm. Anther color: Close to 145B. Amount of pollen: Scarce. Pollen color: Close to 145B. Gynoecium: Quantity per flower: Five. Style length: Less than 1 mm. Style color: Close to 145B. Stigma appearance: Globose. Stigma color: Close to 145B. Ovary color: Close to 145B.

*Seeds*.—Length: Less than 1 mm. Diameter: Less than 1 mm. Color: Brown.

Garden performance: Plants of the new *Spiraea* have been observed to have good garden performance and to tolerate rain, wind and temperatures ranging from about −25° C. to about 34° C.

Pathogen & pest resistance: Plants of the new *Spiraea* have not been observed to be resistant to pathogens and pests common to *Spiraea* plants.

It is claimed:

1. A new and distinct *Spiraea* plant named 'Verspi 1' as illustrated and described.

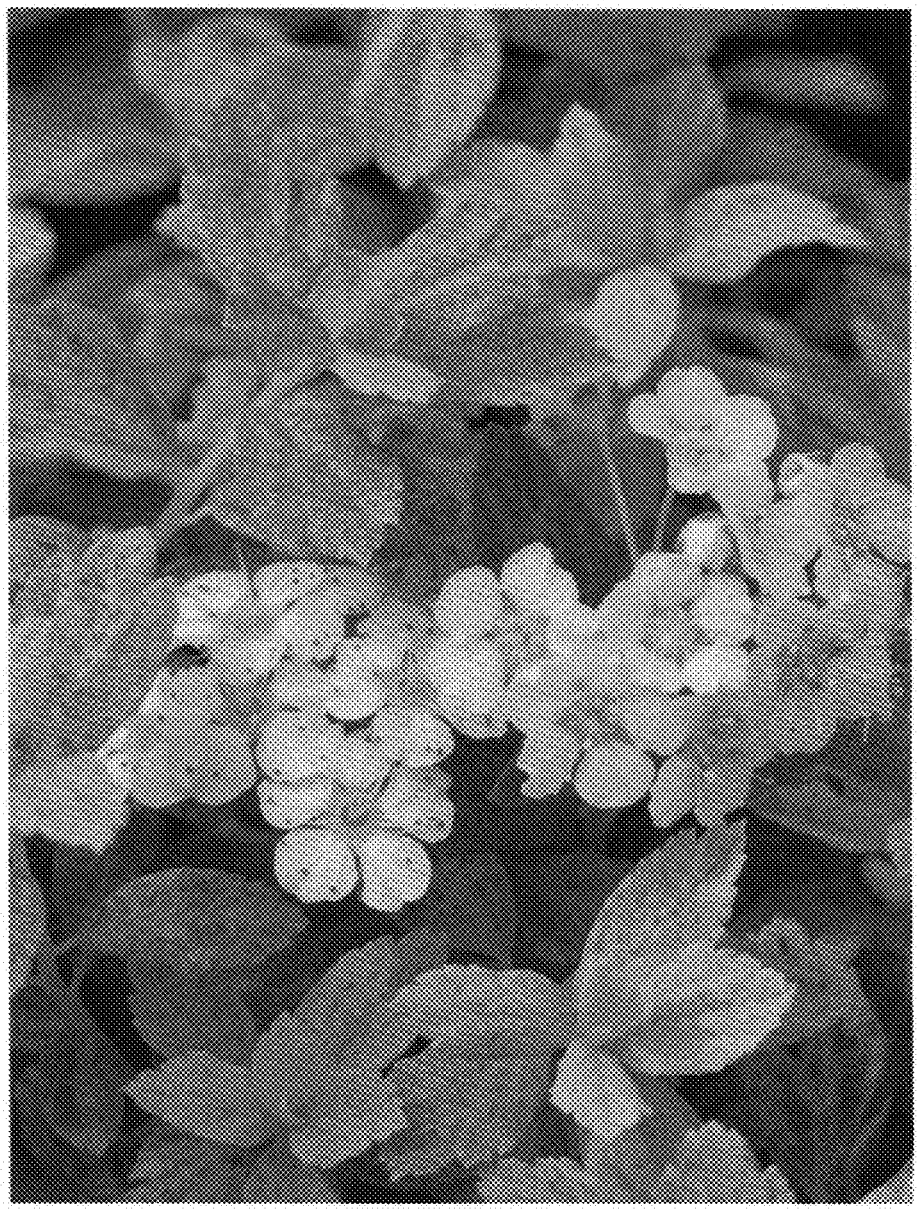

* * * * *